US00PP25015P3

(12) United States Plant Patent
Sato et al.

(10) Patent No.: US PP25,015 P3
(45) Date of Patent: Oct. 28, 2014

(54) **NEW GUINEA *IMPATIENS* PLANT NAMED 'SAKIMP030'**

(50) Latin Name: ***Impatiens hybrida hort* (*I. hawkeri*)**
Varietal Denomination: SAKIMP030

(71) Applicant: Sakata Seed Corporation, Yokohama (JP)

(72) Inventors: Chihiro Sato, Nagano (JP); Shinji Minemura, Nagano (JP)

(73) Assignee: Sakata Seed Corporation, Yokohama (JP)

( * ) Notice: Subject to any disclaimer, the term of this patent is extended or adjusted under 35 U.S.C. 154(b) by 50 days.

(21) Appl. No.: 13/694,617

(22) Filed: Dec. 17, 2012

(65) Prior Publication Data

US 2014/0173796 P1 Jun. 19, 2014

(51) Int. Cl.
*A01H 5/00* (2006.01)

(52) U.S. Cl.
USPC ..... Plt./318.7

(58) Field of Classification Search
USPC ..... Plt./317, 318.7, 318.1
See application file for complete search history.

*Primary Examiner* — Kent L Bell
(74) *Attorney, Agent, or Firm* — Barbara Campbell; Cochran Freund & Young LLC

(57) ABSTRACT

A New Guinea *Impatiens* plant particularly distinguished by having a red flower color, strong root system and a compact plant growth habit is disclosed.

1 Drawing Sheet

Genus and species: *Impatiens hybrida hort* (*I. Hawkeri*).
Variety denomination: 'SAKIMP030'.

BACKGROUND OF THE NEW PLANT

The present invention comprises a new and distinct cultivar of New Guinea *Impatiens*, botanically known as *Impatiens hybrida hort* (*I. Hawkeri*), and referred to by the variety name 'SAKIMP030'. *Impatiens* variety 'SAKIMP030' originated from a hybridization between the female *Impatiens* line 'NF-572A2', an unpatented proprietary *Impatiens* breeding line with an orange flower color and the male *Impatiens* line 'NG-434', an unpatented proprietary *Impatiens* breeding line with a red flower color in Misato, Japan.

In December 2007, the female parent line 'NF-572A2' and the male parent line 'NG-434' were crossed and a population of $F_1$ plants was created. The $F_1$ plants were evaluated in Misato, Japan in an open field trial. The criteria for plant selection included a beautiful red flower color, strong root system and a compact plant growth habit. At the completion of the trial, one single-plant selection was made based on the aforementioned criteria and vegetatively propagated. From May 2009 to August 2009, the selection was evaluated in an open field in Misato, Japan. The selection subsequently was named 'SAKIMP030'. The selection has been asexually propagated by means of vegetative cuttings at Salinas, Calif., and has been found to retain all of its unique characteristics and reproduces true to type in successive generations through such vegetative propagation.

Plant Breeder's Rights for this cultivar have been applied for in Japan as application No. 27419, filed on Sep. 20, 2012.

SUMMARY

The following are the most outstanding and distinguishing characteristics of this new variety when grown under normal horticultural practices in Salinas, Calif.

1. Red flower color;
2. Strong root system; and
3. A compact plant growth habit.

DESCRIPTION OF THE PHOTOGRAPHS

This *Impatiens* plant is illustrated by the accompanying photographs which show the plant's overall plant habit including form, foliage, and flowers. The photographs are of a four-month-old plant grown in Salinas, Calif. under greenhouse conditions in the spring of 2012. The colors shown are as true as can be reasonably obtained by conventional photographic procedures.

DESCRIPTION OF THE NEW VARIETY

Figure 1:
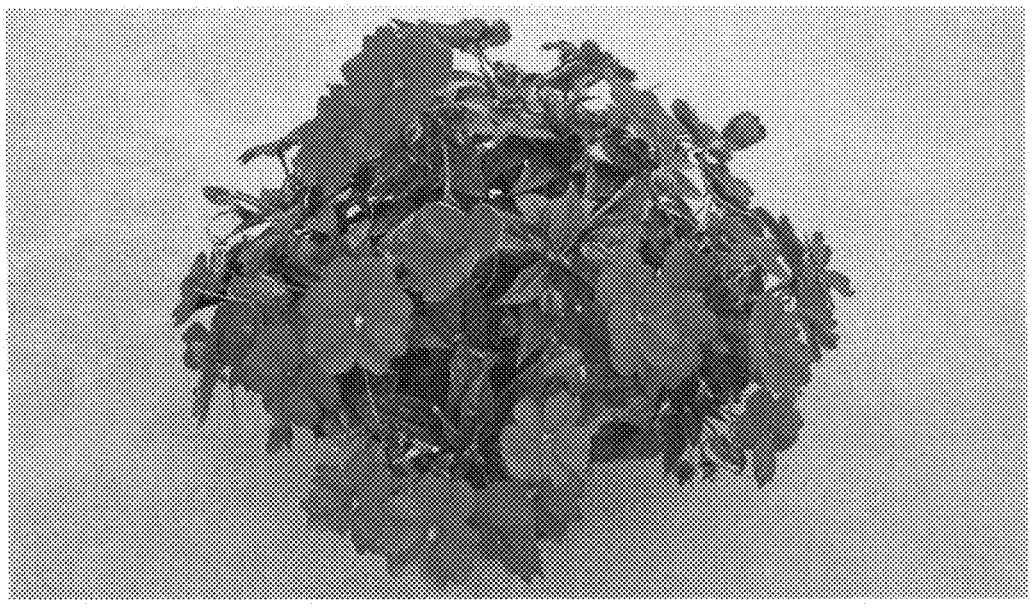
FIG. 1 shows the overall plant habit of the plant grown in a pot.
Figure 2:
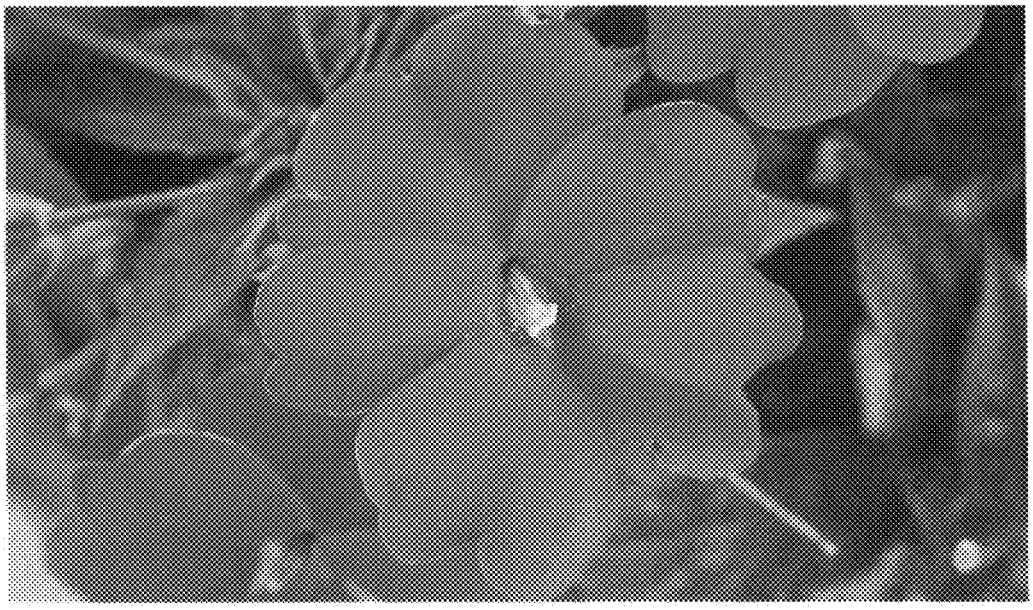
FIG. 2 shows the mature inflorescence of the plant.

The following detailed descriptions set forth the distinctive characteristics of 'SAKIMP030'. The data which define these characteristics were collected from asexual reproductions carried out in Salinas, Calif. Data was collected on four-month-old plants grown under greenhouse conditions in Salinas, Calif. in the summer of 2012. Color references are to The R.H.S. Colour Chart of The Royal Horticultural Society of London (R.H.S.), $4^{th}$ edition (2001).

Classification:

*Family*.—Balsaminaceae.

*Botanical*.—*Impatiens* interspecific cross (*Impatiens hybrida hort*) (*I. Hawkeri*).

*Common*.—*Impatiens*.

*Designation*.—'SAKIMP030'.

Parentage:

*Female parent*.—Proprietary *Impatiens* plant line 'NF-572A2' (unpatented).

*Male parent*.—Proprietary *Impatiens* plant line 'NG-434' (unpatented).

Growth:

*Time to produce a rooted cutting.*—About 4 weeks.

*Environmental conditions for plant growth.*—The terminal 1.0 to 1.5 inches of an actively growing stem was excised. The vegetative cuttings were propagated in five to six weeks. The base of the cuttings were dipped for 1 to 2 seconds in a 1:9 solution of Dip 'N Grow (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 6-inch plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Plants were fertilized every 2 to 3 days, 2 times in consecutive applications and then given one clear water application. Pots were top-dressed with a dry, slow release fertilizer containing 14% nitrogen, 14% phosphorus and 14% potassium. The typical average air temperature was 24° C.

*Time to bloom from propagation.*—6 to 8 weeks.

Plant description:

*Habit.*—Compact.

*Life cycle.*—Tender perennial.

*Height (from soil line to top of foliage).*—14.0 cm.

*Spread.*—40.0 cm.

*Flowering requirements.*—Will flower so long as temperature is above 5° C.

*Temperature tolerances.*—Plants observed to continue flowering in a temperature range of 5° C. to 36° C. Plants can withstand high heat and humidity.

Branches:

*Number of branches.*—3 main branches, 6 branches total.

*Length of branches.*—Approximately 2.0 cm from soil line to first node, approximately 11.0 cm total.

*Diameter of branches.*—1.5 cm, main branch.

*Color of branches.*—RHS 187A (Greyed-Purple).

Stems:

*General.*—Strong; circular cross-section, smooth and shiny.

*Stem length.*—5.0 cm.

*Diameter.*—0.6 cm.

*Internode length.*—2.5 cm.

*Color.*—RHS 187A (Greyed-Purple).

*Pubescence.*—None.

*Anthocyanin color.*—Absent.

Leaves:

*Arrangement.*—Whorled with up to 5 leaves per node, opposite if only two leaves at one node.

*Shape.*—Lanceolate, curled.

*Apex.*—Acuminate.

*Base.*—Attenuate.

*Margin.*—Ciliate.

*Venation.*—Pinnate.

*Venation color.*—Upper vein color: RHS 145C (Yellow-Green). Lower vein color: RHS 145C (Yellow-Green).

*Variegation.*—Absent.

*Surface appearance (both surfaces).*—Dull, waxy.

*Surface pubescence (both surfaces).*—Very slight.

*Surface pubescence color (both surfaces).*—RHS N155A (White).

*Length.*—8.0 cm.

*Width.*—3.5 cm.

*Color.*—Upper surface: Darker than RHS 147A (Yellow-Green). Lower surface: RHS 147B (Yellow-Green).

*Petiole.*—Length: 0.5 cm. Diameter: 0.2 cm. Color: RHS 145C (Yellow-Green) with slight RHS 187D (Greyed-Purple) anthocyanin. Texture: Smooth, glabrous.

*Fragrance.*—Absent.

Flowers:

*Total number of flowers per node.*—1 to 3 in bloom, about 4 to 6 flower buds per node.

*Total number of flower per plant.*—Approximately 40 to 50 in bloom.

*Inflorescence type.*—Single flower with spur.

*Lastingness of individual blooms on the plant.*—14 days.

*Fragrance.*—Absent.

Flower buds:

*Bud surface.*—Glabrous.

*Bud length.*—1.8 cm.

*Bud diameter.*—1.0 cm.

*Bud shape.*—Deltoid, longitudinal cross-section.

*Bud color.*—RHS 187C (Greyed-Purple) with RHS 143C (Green) at edge.

Peduncle:

*Peduncle length.*—4.5 cm.

*Peduncle diameter.*—0.2 cm.

*Peduncle color.*—RHS 61B (Red-Purple).

*Peduncle texture.*—Smooth, glabrous.

Corolla:

*Shape.*—Roughly circular with 5 radial petals.

*Diameter.*—Approximately 6.0 cm.

*Depth.*—0.5 cm to 1.0 cm.

*Petals.*—Shape: Obcordate. Apex: Emarginate (cleaved). Margin: Entire. Base: Attenuate. Pubescence: Glabrous. Length: 3.0 cm. Width: 3.0 cm. Color: Upper: Closest to but darker than RHS 45A (Red). Lower: Closest to but darker than RHS 58B (Red-Purple). Eye zone: RHS 187B (Greyed-Purple) and RHS 187D (Greyed-Purple).

Spur:

*Shape.*—Tubular; curved downward.

*Length.*—8.0 cm.

*Diameter.*—0.2 cm.

*Color.*—RHS 61B (Red-Purple).

Calyx:

*Arrangement.*—Composed of 2 sepals.

*Sepals.*—Shape: Lanceolate. Base: Subcordate. Apex: Caudate. Margin: Entire. Texture: Glabrous. Color: RHS 187C (Greyed-Purple) with RHS 143B (Green) at tip. Length: 1.5 cm. Diameter: 0.8 cm.

Reproductive organs:

*Stamen number.*—Many.

*Stamen form.*—Fused; split into 4 lobes.

*Filament length.*—0.4 cm.

*Anther length.*—0.9 cm.

*Stamen color.*—Anther color: RHS 155A (White). Filament color: RHS 187A (Greyed-Purple).

*Pollen color.*—RHS 155D (White).

*Pollen amount.*—Abundant.

*Pollen description.*—Powdery.

*Ovary.*—Parietal.

*Ovary surface color.*—RHS 145A (Yellow-Green).
*Pistil number.*—5.
*Pistil length.*—0.4 cm.
*Stigma color.*—RHS 143A (Green).
*Style length.*—1.0 cm.
*Style color.*—RHS 143A (Green).
*Seed production.*—Absent.

Disease and insect resistance: No particular resistance or susceptibility observed.

COMPARISON WITH PARENTAL LINES AND KNOWN VARIETY

'SAKIMP030' is a new and unique variety of *Impatiens* owing to its red flower color, strong root system and a compact plant growth habit. 'SAKIMP030' is distinguished from its parents mainly by flower color as shown in Table 1 below:

TABLE 1

Comparison with Parental Lines

| Characteristic | 'SAKIMP030' | Female Parent 'NF-572A2' | Male Parent 'NG-434' |
|---|---|---|---|
| Plant growth habit | Compact | Information not available | Less compact than 'SAKIMP030' |
| Branching | Good branching: 3 main branches, 6 branches total | Information not available | Less branching than 'SAKIMP030' |
| Flower color | Bright red | Orange | Red |

'SAKIMP030' is a new and unique variety of *Impatiens* owing to its red flower color, strong root system and a compact plant growth habit. 'SAKIMP030' is most similar to the commercial *Impatiens* variety 'Misato FG1' (U.S. Plant Pat. No. 17,708), commercially known as SunPatiens® 'Vigorous Red'; however there are differences in the flower color as described in the table below (color references are to The Royal Horticultural Society Colour Chart, 4th edition):

TABLE 2

Comparison with Similar Variety

| Characteristic | 'SAKIMP030' | 'Misato FG1' |
|---|---|---|
| Petal color, upper surface | Closest to but darker than RHS 45A (Red) | Closest to RHS 46C (Red) |
| Petal color, lower surface | Closest to but darker than RHS 58B (Red-Purple) | RHS 58C (Red-Purple) |
| Petal color, eye zone | RHS 187B and RHS 187D (Greyed-Purple) | RHS 60D (Red-Purple) |
| Plant growth habit | Compact | Vigorous |

We claim:

1. A new and distinct cultivar of New Guinea *Impatiens* hybrid plant as shown and described herein.

* * * * *